United States Patent
Helibronn

(10) Patent No.: US 7,037,723 B1
(45) Date of Patent: May 2, 2006

(54) RECOMBINANT HERPES VIRUSES FOR PREPARING RECOMBINANT ADENO-ASSOCIATED VIRUSES

(75) Inventor: Regine Helibronn, Berlin (DE)

(73) Assignee: Applied Genetic Technologies Corporation, Alachua, FL (US)

( * ) Notice: Subject to any disclaimer, the term of this patent is extended or adjusted under 35 U.S.C. 154(b) by 0 days.

(21) Appl. No.: 09/720,252

(22) PCT Filed: Sep. 1, 1998

(86) PCT No.: PCT/EP98/05542

§ 371 (c)(1),
(2), (4) Date: Apr. 12, 2001

(87) PCT Pub. No.: WO00/01834

PCT Pub. Date: Jan. 13, 2000

(30) Foreign Application Priority Data

Jul. 6, 1998 (DE) ................................ 198 30 141

(51) Int. Cl.
C12N 15/35 (2006.01)
C12N 15/38 (2006.01)
C12N 15/63 (2006.01)
C12N 15/864 (2006.01)
C12N 15/869 (2006.01)

(52) U.S. Cl. ................ 435/457; 435/320.1; 435/235.1; 435/455; 435/456

(58) Field of Classification Search ............... 536/23.1, 536/24.1; 435/325, 320.1, 235.1, 629, 91.4
See application file for complete search history.

(56) References Cited

U.S. PATENT DOCUMENTS 5,994,116 A * 11/1999 Dargan et al. .............. 435/236
6,686,200 B1 * 2/2004 Dong et al. ................. 435/457

FOREIGN PATENT DOCUMENTS

WO 95 06743 3/1995
WO 95 02671 8/1995

OTHER PUBLICATIONS

Rixon et al., "Insertion of DNA sequences at a unique restriction enzyme site engineered for vector purposes into the genome of herpes simplex virus type 1", Journal of Virology, vol. 113, No. 71, Jan. 1, 1990, pp. 2931.

Srvuastava et al., "Nucleotide Sequence and Organization of the Adeno-Associated Virus 2 Genome", Journal of General Virology, vol. 45, No. 2, Feb. 1, 1983, pp. 555-564.

Conway et al., "Recombinant adeno-associated virus type 2 replication and packaging is entirely supported by herpes simplex virus type 1 amplicon expressing rep and cap", Journal of Virology, vol. 71, No. 11, Nov. 1997, pp. 8780-8789.

Carter, "Adeno-Associated Virus Vectors", Current Opinion in Biotechnology, 1992, 3: pp. 533-539.

Muzyczka, "Use of Adeno-Associated Virus as a General Transduction Vector for Mammalian Cells", Current Topics in Microbiology and Immunology, vol. 158, 1992, pp. 97-129.

Samulski, et al., "Helper-Free Stocks of Recombinant Adeno-Associated Viruses: Normal Integration Does Not Require Viral Gene Expression", Journal of Virology, Sep. 1989, vol. 63, (9), pp. 3822-3828.

McGeoch, et al., "DNA Sequence of the Herpes Simplex Virus Type 1 Gene Encoding glycoprotein gH, and Identification of Homologues in the Genomes of Varicella-Zoster Virus and Epstein-Barr Virus", Nucleic Acids Research, vol. 14, (10), 1986, pp. 4281-4292.

Weindler, et al., "A Subset of Herpes Simplex Virus Replication Genes Provides Helper Functions for Productive Adeno-Associated Virus Replication", Journal of Virology, May 1991, vol. 65, (5), pp. 2476-2483.

Gossen and Bujard, "Tight Control of Gene Expression in Mammalian Cells By Tetracycline-Responsive Promoters", Proc. Natl. Acad. Sci USA (1992), vol. 89, pp. 5547-5551.

No, et al., "Ecdysone-Inducible Gene Expression in Mammalian Cells and Transgenic Mice", Proc. Natl. Acad. Sci. USA, 1996, vol. 93, pp. 3346-3351.

(Continued)

Primary Examiner—David Guzo
(74) Attorney, Agent, or Firm—Edwards Angell Palmer & Dodge LLP

(57) ABSTRACT

The invention relates to a recombinant herpes virus which contains the rep and cap genes of the adeno-associated virus, and to a method for producing high-titer, highly infectious adeno-associated virus vector preparations.

14 Claims, 6 Drawing Sheets

OTHER PUBLICATIONS

Stoker, et al., "Syrian Hamster Fibroblast Cell Line BHK21 and Its Derivatives", Nature 203, 1964, No. 4952, pp. 1355-1357.

Samulski, et al., "A Recombinant Plasmid from Which an Infectious Adeno-Associated Virus Genome Can Be Excised in Vitro and Its Use to Study Viral Replication", Journal of Virology, 1987, vol. 61 (10), pp. 3096-3101.

Laemmli, "Cleavage of Structural Proteins during the Assembly of the Head of Bacteriophage T4", Nature, 1970, vol. 227, pp. 680-685.

Kleinschmidt, et al., "Sequence Elements of the Adeno-Associated Virus rep Gene Required for Suppression of Herpes-Simplex-Virus-Induced DNA Amplification", Virology 206 (1995), pp. 254-262.

Wistuba, et al., "Intermediates of Adeno-Associated Virus Type 2 Assembly: Identification of Soluble Complexes Containing Rep and Cap Proteins", Journal of Virology, 1995, vol. 69 (9), pp. 5311-5319.

Wistuba, et al., "Subcellular Compartmentalization of Adeno-Associated Virus Type 2 Assembly", Journal of Virology, 1997, vol. 71 (2), pp. 1341-1352.

Zolotukhin, et al., A "Humanized" Green Fluorescent Protein cDNA Adapted for High-Level Expression in Mammalian Cells, Journal of Virology, 1996, vol. 70 (7), pp. 4646-4654.

Church, et al., Genomic Sequencing, Proc. Natl. Acad. Sci.USA, 1984, Biochemistry, vol. 81, pp. 1991-1995.

* cited by examiner

A.

B.

Rep antibody   (76.3)

Cap antibody   (B1)

Capsid antibody   (A20)

RECOMBINANT HERPES VIRUSES FOR PREPARING RECOMBINANT ADENO-ASSOCIATED VIRUSES

The invention relates to a recombinant herpesvirus, to a process for preparing it and to a process for producing high-titer, infectious adeno-associated virus vector preparations.

A large number of genetic diseases are known for which no effective therapy has so far been found. One possible way of treating genetic diseases is that of introducing a defined gene, which is able to correct the genetic disease, into the genome of the patient such that it is present in the DNA of the patient and can replicate in this DNA.

Vectors can be used for introducing the desired correcting gene into the cell, with viral vectors based on adeno-associated viruses (AAV) exhibiting a number of advantages for gene therapy as compared with other viral vector systems. AAV is a very stable but nonpathogenic virus. Furthermore, it has a broad tissue tropism and the ability to integrate efficiently to the chromosome in both proliferating and resting cells.

The viral vector systems employed are, for the most part, AAV vectors which are based on adeno-associated virus type 2 (AAV-2) (Carter, Curr. Opinion. Biotech. 3 (1992) 533; Muzyczka, Curr. Top. Microbiol. 1 mm. 158 (1992) 97). AAV-2 is a widely distributed human virus, with no pathogenicity being induced in association with the primary infection, which in the main occurs in childhood. Nor are there any indications that AAV-2 might possess any oncogenic potential. Because AAV-2 is highly stable, the virus can also withstand elaborate purification methods without any loss of infectivity.

AAV-2 is a small, single-stranded DNA virus which carries two genes: the rep gene encodes four overlapping regulatory proteins, i.e. Rep78 and Rep52 and C-terminally spliced variants of the two proteins, i.e. Rep68 and Rep40. The Rep proteins are used for AAV gene regulation, DNA replication and virus packaging. The cap gene encodes the three virus capsid proteins. The two genes rep and cap are flanked by 145 bp inverted repeats which serve as origins of replication. These are the only AAV DNA sequences which are required in cis for DNA replication, virus packaging and integration into the host cell genome, which means that foreign sequences of approx. 4.7 kb in length can be cloned into each respective vector.

AAVs are replication-defective and, in order to be able to replicate efficiently, require to be coinfected with a helper virus. Without helper viruses being present, AAV integrates with high frequency into the host cell genome, with a specific locus on chromosome 19 (q13.3-qter) being highly preferred. This integration is independent of viral or cellular DNA replication. Because of the abovementioned advantages, AAV vectors offer ideal preconditions for introducing genes into nonproliferating cells and stably integrating them in these cells. Recombinant AAV vectors which contain a heterologous DNA which encodes a desired gene product are generally used for gene therapy. However, inserting the heterologous DNA into the AAV vectors impairs expression of rep and cap. For this reason, these proteins, or systems which express these proteins, have to be supplied from the outside in order for the recombinant AAV vectors to be replicated.

This replication can be effected, for example, by cotransfecting adenovirus-infected cells with the recombinant AAV vector and a helper plasmid in which the AAV rep and cap genes are flanked by the adenovirus type 5 origins of replication. The helper plasmid is replicated in the adenovirus-infected cells such that sufficient quantities of rep and cap are available for propagating the AAV vector. The construct expressing rep and cap does not possess any DNA sequences in common with the AAV vector, which means that no wild-type AAV, which would contaminate the vector preparation, can be formed as a result of homologous recombination (Samulski et al., J. Virol. 63 (1989), 3822). However, a disadvantage of this system is that the virus titers which can be achieved are, at from $10^4$ to $10^6$ infectious particles per ml, markedly lower than in the case of wild-type AAV, which can achieve titers of up to $10^{12}$ particles per ml. Moreover, for each batch, cells have to be cotransfected afresh with the AAV vector and the rep- and cap-expressing helper plasmid, and then infected with adenovirus, since the helper plasmid is not packaged as virus and can consequently not be transmitted by infection.

J. Conway et al. (J. Virol. 71 (11) (1997), 8780–8789) describe a method for replicating and packaging recombinant AAV type 2 using a herpes simplex virus (HSV) type 1 amplicon which expresses Rep and Cap. The HSV amplicons are packaged in HSV envelopes and can therefore only be replicated in the presence of wild-type HSV. When they are being replicated together, it is not possible to predict the relative ratio of wild-type HSV and packaged amplicons, and it is scarcely possible to adjust this ratio, either. Nor is there any method for separating the two virus populations from each other by purification, since the envelope, which is common to the two populations, determines the main physicochemical properties. In addition to this, there is the problem that, because of growth disadvantages, the amplicon is already present in only a small quantity, which can no longer be detected, after only a few passages. The amplicon system can therefore only be used reproducibly when, for each rAAV preparation, the amplicon plasmid is transfected, followed by superinfection with wild-type HSV. However, the consequence of this is that the amplicon plasmids have to be transfected afresh for each round of replication, something which is, however, precisely the disadvantage of the packaging system which is described above.

An attempt was made to resolve the disadvantages associated with using non-selfreplicating plasmids by establishing stable cell lines which express the rep and cap AAV genes in sufficiently high quantity. However since Rep is toxic, it is very difficult to produce stable cell clones which express functional Rep78 or Rep68.

WO 95/06743 describes a process for preparing recombinant AAV in which the helper virus employed is an adenovirus construct which contains a recombinant insert possessing the AAV rep and cap genes. However, the expression of Rep proteins in AAV-infected cells inhibits infection with adenovirus so that it is not possible to obtain any high-titer preparations. WO 95/06743 also proposes using a herpesvirus vector in place of the adenovirus vector. However, it does not provide any reworkable instruction as to how to prepare stable recombinant herpesviruses which contain AAV gene regions in which there is no reversion to the wild type.

One object of the invention was, therefore, to provide a system which can be used to prepare recombinant AAV vectors as the high-titer preparations which are required for applications on a clinical scale. Another object of the invention was to make available a helper construct for replicating AAV vectors, in which construct the disadvantages of the state of the art are at least partially eliminated.

According to the invention, these objects are achieved by means of stable cell lines which express the AAV rep and cap genes in sufficiently high quantity and in which AAV vectors can be propagated by infection.

The invention relates to a recombinant herpesvirus which contains a rep gene and a cap gene which are derived from adeno associated viruses (AAVs), for example a rep gene and a cap gene which are derived from AAV-2, or a gene which is functionally equivalent thereto, which are operatively linked to an expression control sequence. Preferably, the rep and cap genes are present on an insert which is integrated at a suitable site in the genome of the herpesvirus.

The recombinant herpesvirus according to the invention contains, on the one hand, the helper functions which are required for efficiently replicating AAV and can, in addition, express the AAV regions encoding Rep and Cap in sufficient quantity to enable AAV vectors to be replicated and packaged in cell culture when they are coinfected with the recombinant HSV (rHSV).

Suitable expression control sequences are all those sequences which lead to adequate expression of rep and cap in the target cell, for example homologous AAV expression control sequences, such as the AAV p5 promoter, or heterologous promoters, e.g. eukaryotic cellular or viral promoters. Constitutive or regulatable expression control sequences can be used. The rep and cap genes can be under the joint control of a single expression control sequence, or each of the genes can be under the control of a separate, identical or different, expression control sequence.

It has been observed, surprisingly, that herpesviruses, in particular HSV, are resistant to a high expression of the AAV Rep proteins. By integrating the rep gene and the cap gene into a herpesvirus, which is in any case required as a helper virus for replicating the helper virus-dependent AAV vectors, it was possible to obtain a construct which exhibits all the functions which are required for AAV replication and which makes it possible to prepare, in large quantities, the AAV proteins which are required for propagating the vector. Using such a system, it is possible to prepare infectious AAV vectors on a large scale, as they are required for gene therapy on a clinical scale. The formation of recombinant AAV is consequently no longer dependent on transfection efficiencies, as is the case when using plasmids.

The herpesvirus according to the invention is genetically stable and preferably does not exhibit any reversion to the wild type. Thus, no visible reversion to the wild type is seen even after several consecutive dilution steps in a plaque purification, for example after 3, preferably after 5, and particularly preferably after 7, dilution steps, thereby demonstrating that the integrated cassette remains stable. Another advantage of the herpesvirus according to the invention is that it can be cultured to a high titer, e.g. to a titer of $\geq 5\%$, in particular $\geq 10\%$, and particularly preferably $\geq 20\%$ of the titer of the corresponding wild type herpesvirus, with the titer in this connection preferably being determined as a cell release virus (CRV) titer.

The recombinant herpesvirus according to the invention preferably also contains a reporter gene whose expressibility is associated with integration of the rep and cap genes. The reporter gene is operatively linked to a suitable expression control sequence, such as an SV40 promoter or another promoter, e.g. an HSV promoter or AAV promoter. Preference is given to the reporter gene being a gene which is not a gene for resistance to an antibiotic, particularly preferably a gene which encodes a polypeptide which is directly, e.g. visually, detectable, e.g. LacZ or GFP (green fluorescence protein). The purity of AAV preparations, which would no longer contain the recombinant herpesvirus, can be monitored by expressing the reporter gene. This furthermore makes it also possible to monitor the purity of recombinant herpesvirus preparations with regard to contamination with wild type herpesviruses.

In principle any member of the herpesvirus family (Herpesviridae) can be converted into a recombinant herpesvirus according to the invention by inserting an AAV rep gene and an AAV cap gene. Examples of suitable herpesviruses are herpes simplex virus (HSV), cytomegalovirus (CMV), pseudorabies virus (PRV) and Epstein-Barr virus (EBV). Particular preference is given to herpes simplex virus (HSV) and, in particular, HSV type I. Advantageously, use is made of a herpesvirus which possesses a unique restriction site, e.g. the HSV type I mutant 1802 (Rixon et al., J. Gen. Virol. 71 (1990), 2934–2939), which possesses only one unique XbaI site in the Us region at position 143 969 (the positions are numbered in accordance with McGeoch et al., Nucl. Acids Res. 14 (1986), 1727–1745).

The herpesvirus can contain the AAV rep gene and the AAV cap gene in a nonessential region, e.g. in the $U_S$ and/or the $U_L$ region(s). Preference is also given to using replication-deficient herpesvirus mutants. To obtain such mutants, the rep gene and/or the cap gene can be inserted into a region of the herpesvirus genome which is required for replicating the herpesvirus but which is not required for AAV replication.

Alternatively, use can be made of a herpesvirus mutant in which the corresponding herpesvirus replication gene has already been deleted from the outset. An example of a suitable gene for this purpose is the UL9 gene, which is absolutely essential for HSV replication but which is superfluous for AAV replication (Weindler et al., J. Virol. 65 (1991), 2476–2483). In addition to this, the UL54 gene, which encodes the immediate early protein ICP27, is also suitable. This gene is not required for AAV replication, either. While deletion of the UL54 gene leads to the herpesvirus replication cycle being slowed down, the corresponding mutant is not completely replication-deficient, in contrast to a mutation in the UL9 gene. In addition to this, other herpesvirus genes whose mutation and/or deletion has (have) the same effect, namely a deceleration or a complete blockage of the herpesvirus replication cycle are also suitable for the insertion in question.

Preferably, the recombinant herpesvirus does not contain the complete AAV inverted repeat sequence (ITR), and is particularly preferably completely free of AAV ITR sequence moieties.

An additional improvement can be achieved by using regulatable expression control sequences for the rep gene and/or the cap gene, in particular for the rep gene. Examples of these expression control sequences are those which can be regulated by adding tetracycline (Gossen and Bujard, Proc. Natl. Sci. USA (1992), 5547–5551) or by adding ecdysone (No et al., Proc. Natl. Acad. Sci. USA (1996), 3346–3351). Alternatively, it is also possible to use promoters which control the expression of early and late herpesvirus proteins, e.g. derived from HSV.

The invention furthermore relates to a process for preparing a recombinant herpesvirus, wherein the AAV rep gene and the AAV cap gene are stably integrated into the genome of a herpesvirus. For this, the herpesvirus DNA is preferably cleaved at one or more desired sites, and a DNA fragment, e.g. a plasmid, containing the rep gene and the cap gene is ligated into the herpesvirus DNA. The cleavage is preferably carried out using restriction enzymes, for example using XbaI. Alternatively, the rep and cap genes can also be inserted into the herpesvirus genome by means of homologous recombination. The rep-cap construct must then possess flanking sequences which match, or at least exhibit a high degree of homology with, the DNA sequence which is earmarked for the insertion into the herpesvirus genome.

The invention furthermore relates to a nucleic acid which is derived from a recombinant herpesvirus according to the invention and which contains the adeno associated virus (AAV) rep gene and the adeno associated virus cap gene, and also the helper functions which are derived from a herpesvirus and which are required for replicating recombinant adeno associated virus vectors, in each case operatively linked to expression control sequences. This nucleic acid is preferably located on a vector, in particular on a eukaryotic vector.

The invention furthermore encompasses a virus composition which comprises the recombinant herpesvirus according to the invention. Such a composition is, in particular, free of wild type herpesvirus.

The term virus, as used in this document, is also to be understood as meaning virions.

The recombinant herpesviruses and vectors according to the invention are advantageously used for preparing hightiter, infectious rAAV vector preparations. The invention therefore encompasses a process for preparing infectious AAV vector preparations, which process comprises the steps of:
(a) preparing a viral vector which is based on adeno associated viruses (AAVs) and which contains a heterologous DNA insertion,
(b) preparing a recombinant herpesvirus which contains an AAV rep gene and an AAV cap gene operatively linked to an expression control sequence,
(c) introducing the AAV vector from (a) and the recombinant herpesvirus from (b) into a cell, e.g. by means of infection and/or DNA transfection,
(d) replicating the AAV vector, and
(e) obtaining an infectious AAV vector preparation.

Instead of the recombinant herpesvirus (or virion), it is also possible to employ a corresponding vector which contains the AAV rep gene and the AAV cap gene and also the helper functions which are necessary for replicating and packaging AAV.

Preference is given to transfecting or infecting the cell with the recombinant AAV vector and then infecting it with the recombinant herpesvirus. Particular preference is given to introducing both the AAV vector and the herpesvirus into the cell by infection since it is possible, in this way, to suppress, as far as possible, the occurrence of an unwanted illegitimate recombination. It is possible to use a replicatable recombinant herpesvirus for the process according to the invention. However, preference is given to employing a recombinant herpesvirus which is not replicatable or which is only replicatable to a limited extent, with this thereby leading to a further increase in the yield of AAV. It is possible to use the process according to the invention to obtain high-titer, infectious AAV vector preparations, in particular encapsulated rAAV preparations.

Using the recombinant herpesvirus (virion) or vector according to the invention, which comprise the helper functions which are required for AAV replication and provide an adequate quantity of Rep and Cap proteins, it is possible to replicate AAV vectors by infecting eukaryotic cells, including a variety of generally available cell lines. The invention furthermore relates, therefore, to a cell which contains a recombinant herpesvirus or vector according to the invention. The cell is preferably a mammalian cell, in particular a cell which can be cultured on a permanent basis. Examples are rodent cells, such as BHK cells, e.g. BHK21. However, it is also possible to use other cells, e.g. human cells such as Vero cells or HeLa cells.

The cell can contain the virus, the vector or the virion in extrachromosomal form, in one or more copies. Cells of this nature can, for example, be obtained by infection. Alternatively, the virus, the vector or the virion can also be present in integrated form in the genome of the cell. The cell is preferably generated by infecting it with the virus.

In addition to this, the cell can also contain a recombinant AAV vector, in particular an AAV vector which contains a heterologous DNA insert which encodes a therapeutically active polypeptide. The AAV vector may be present extrachromosomally or integrated latently in the genome of the cell. It is then released when the cell is infected with recombinant herpesvirus and then replicates as after an infection with AAV vector.

Infecting mammalian cells with the recombinant herpesvirus according to the invention resulted in a high level of expression of the rep and cap genes, with the yields being comparable to a coinfection with wild type AAV and a herpes simplex virus.

Finally, the invention also relates to an improved process for producing infectious AAV vector preparations, in which process, as compared with known processes, in which the AAV vector was introduced by transfecting it into a host cell, a significant decrease is found in the occurrence of unwanted illegitimate recombinations. The process comprises introducing an AAV vector and an arbitrary helper virus, e.g. an adenovirus, a herpesvirus and, in particular, a rep/cap-expressing herpesvirus according to the invention, into a cell, culturing the cell under conditions which are suitable for replicating the AAV vector, and obtaining an infectious AAV vector preparation from the cell and/or the culture supernatant, in which process the AAV vector and the helper virus are both introduced into the cell by infection.

The invention is clarified by means of the enclosed figures and the examples which follow.

FIG. 1 shows the genomic structure of an rHSV/AAV according to the invention. The position of the XbaI site in HSV-1 1802, i.e. 143 969, is in conformity with the numbering used by McGeoch et al., Nucl. Acids Res. No. 14 (1986), 1727–1745). The AAV genome is numbered in conformity with the Genbank deposition number J01901.

EXAMPLES

Figure 1:
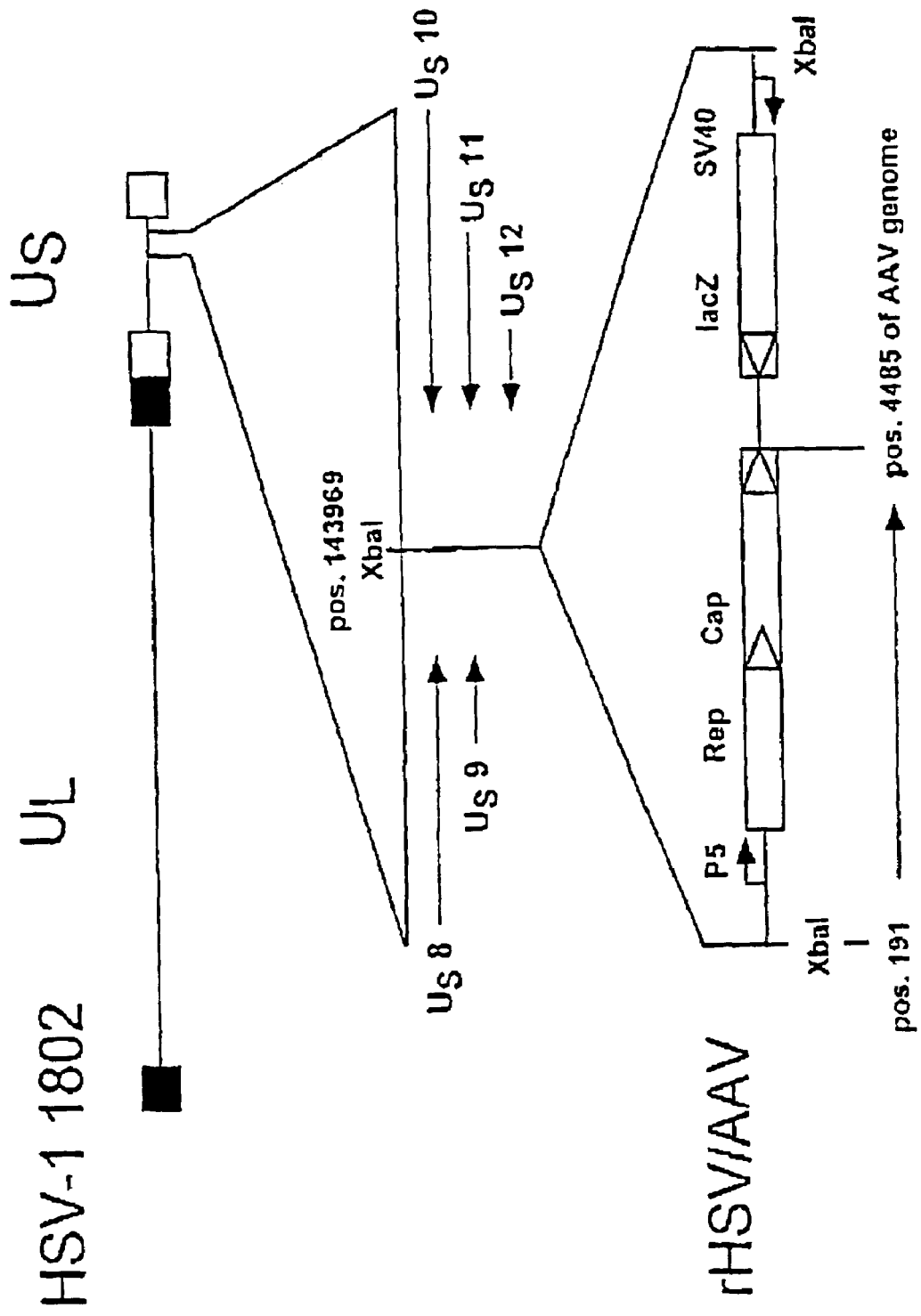

1. Materials and Methods 1.1 Culturing Cells

BHK-21 cells (Stoker et al., Nature, 203 (1964), 1355–1357; ECACC No. 8501143) were cultured, at 37° C. at 5% $CO_2$, as a monolayer in G-MEM (Gibco BRL No. 21710-025) containing 10% NCS (newborn calf serum) (Gibco BRL No. 16010-084), 1×tryptose phosphate broth (Gibco BRL No. 18060-02) and Pen/Strep (Seromed). In order to culture BHK cells in roller bottles (Falcon 850 cm³, No. 3027), a 50 ml volume of medium was used and the bottles were rotated at 0.8 rpm and at 37° C. and 5% $CO_2$. In order to infect growing BHK-21 cells in the roller bottles, the volume was reduced to 15 ml of complete G-MEM. BHK-21 cells were cultured for up to 15 passages before beginning a new culture.

HeLa and Vero cells were cultured in D-MEM (Gibco No. 21855-025) containing 10% FCS (Seromed No. S0115) and Pen/Strep (Seromed).

1.2 Producing Infectious HSV and rHSV Preparations

Wild-type or recombinant herpes simplex viruses (HSVs) were replicated by infecting, at a multiplicity of infection (MOI) of 0.002, approximately $2 \times 10^8$ BHK-21 cells which were being cultured in roller bottles as described in example 1. The course of the infection was monitored by means of the increase in the cytopathic effect (CPE) in the cell culture. Three days after the infection, most of the cells exhibited a complete CPE and could be collected in the cell culture medium by shaking. After centrifuging at 1 500×g and 4° C. for 10 min, the virus was isolated from the cell-free supernatant (CRV; cell-released virus), divided into aliquots and frozen at −80° C.

The cell pellet was resuspended in PBS (phosphate-buffered saline solution) and sonicated for 1 min at 4° C. After centrifuging at 2 000×g and 4° C. for 10 min, the supernatant was isolated as cell-associated virus (CAV), divided into aliquots and frozen at −80° C.

1.3 Purifying HSV Virions

In order to prepare HSV virions, BHK cells which were being cultured in roller bottles were infected as described in 1.2. After centrifuging, the clear, CRV-containing supernatant was transferred into centrifugation tubes. Virions were pelleted by centrifuging at 23 000×g, corresponding to 13 500 rpm when using a Beckman SW28 rotor, and at 4° C. for 2 h.

The virus pellet was resuspended in 1 ml of MEM without phenol red (MEM-PR) and homogenized by sonicating at 4° C. (3× for 30 sec). The suspension was layered onto a linear Ficoll gradient (5%+15% w/v in MEM-PR) in Beckman SW28 Ultraclear tubes and centrifuged at 12 000 rpm (19 000×g) and 4° C. for 2 h.

On illumination, the concentrated virion band was visible in the middle of the tube. It is possible to see a diffuse band, which contains damaged particles, above the virion band. The virion band was collected by puncturing the tube with a 21 or 23 gauge needle, after which it was transferred into a new Beckman SW28 Ultraclear tube and diluted with MEM-PR to a final volume of 35 ml. The virions were then pelleted by centrifuging at 22 200 rpm (65 000×g) and 4° C. for 2 h. The pellet was resuspended in MEM-PR and stored at −80° C. In order to prepare viral DNA, the pellet was resuspended in 300 µl of TE buffer and transferred into a 1.5 ml tube for further processing.

Alternatively, HSV virions were purified using a CsCl gradient.

1.4 Preparing an HSV DNA

SDS (final concentration of 0.2%) and proteinase K (final concentration 300 µg/ml) were added to the virion pellet which had been obtained as described in 1.3 and which had been resuspended in 300 µl of TE. The mixture was incubated at 37° C. for at least 1 h. After sodium acetate, pH 9.2, had been added to a final concentration of 0.3 M, and after a phenol/chloroform extraction (2×phenol/CIA (chloroform-isoamyl alcohol), 1×CIA), the DNA was precipitated by centrifuging after having added 2 volumes of ethanol. The pellet was washed with 70% ethanol, dried and resuspended in TE (tris-EDTA buffer, 10 mM tris HCl, 1 mM EDTA).

1.5 Preparing the Plasmid psub201lac

The plasmid pFJ3, which is based on pCH110 (Pharmacia) and which contains a lacZ gene under the control of an SV40 promoter (Rixon et al., J. Gen. Virol. 71 (1990) 2931–2939), was cleaved with BamHI and dephosphorylated. The XbaI fragment from psub201 (Samulski et al., J. Virol. 61 (1987), 3096–3101), which contains the 191-4485 sequence of adeno-associated virus type 2 (Genbank access No. J019901), including the rep and cap genes and the p5, p19 and p40 promoters but without the inverted terminal repeat (ITR) sequences, was inserted into pFJ3 in order to yield psub201lac.

1.6 Plaque Assay

Subconfluent BHK-21 cells were infected with various dilutions of HSV CRV or CAV preparations. After 1 h of adsorption at 37° C., the cells were washed with PBS and overlaid with G-MEM containing 0.5% Sea Plaque agar, 5% NCS, Pen/Strep and 1×tryptose phosphate broth. After incubating at 37° C. and 5% $CO_2$ for 3 days, the plaques were counted and the titer was determined.

1.7 Staining with X-Gal

Infected or uninfected cells were washed 1× with 150 mM NaCl, 15 mM sodium phosphate, pH 7.3, in PBS. The cells were fixed by incubating them for 5 min in cold PBS containing 2% formaldehyde and 0.2% glutaraldehyde. The cells were washed with PBS in order to remove the fixative. Finally, the cells were overlaid with the X-Gal staining solution containing 1 mg of X-Gal/ml, 5 mM potassium ferrocyanide, 5 mM potassium ferricyanide and 2 mM $MgCl_2$ in PBS. Stained cells were usually incubated at 37° C. for several hours until a blue color was visible.

1.8 Western Blotting

The Western blotting was carried out as described in Laemmli, Nature, 227 (1970) 680–685. The cells were washed 2× with PBS, either while they were still adhering to the dish or after they had been collected and pelleted in a 15 ml tube. After having added 100 µl of 1×SDS sample buffer (50 mM tris-Cl, pH 6.8; 1% β-mercaptoethanol; 2% SDS; 0.1% bromophenol blue; 10% glycerol) per $1 \times 10^5$ cells, the suspension was transferred to a 1.5 ml reaction vessel. The samples were incubated in boiling water for 10 min, cooled on ice and stored at −80° C. For the analysis, up to 30 µl of each sample were added to a 10% SDS polyacrylamide gel (SDS-PAGE). After the electrophoresis, the gel was equilibrated for 15 min in a Tris-glycine solution (25 mM Tris base; 95% mM glycine; 10% methanol). The proteins were transferred to a nitrocellulose membrane (Schleicher and Schuell, BA85, No. 401196) using a semi-dry blotting device and 1 $mA/cm^2$. In order to check the transfer and the quantity of protein, the membrane was stained with Ponceau-S (Sigma). The membrane was blocked, for 30 min at room temperature or overnight at 4° C., in PBS, 0.3% Tween-20, 10% fat-free milk powder.

Antibodies were diluted appropriately in PBS, 0.3% Tween-20, 10% fat-free milk powder and incubated for at least 1 h at room temperature or overnight at 4° C. The monoclonal antibodies 303.9 and 76.3 (diluted 1:10) were used for detecting rep (Kleinschmidt et al. Virology 206 (1995) 254–262; Wistuba et al., J. Virol. 69 (1995), 5311–5319). The antibody B1 (diluted 1:10) was used for detecting the cap (VP) proteins (Wistuba et al. (1995) see above). The filters were washed three times, for 10 min at room temperature, with PBS, 0.3% Tween-20. The antibody A20 (Wistuba et al., J. Virol. 71 (1996), 1341–1352) was used for detecting AAV capsid structures.

The second antibody, which was normally an anti-mouse antibody peroxidase conjugate, was diluted in PBS, 0.3% Tween-20, 10% fat-free milk powder and incubated with the filter for from 30 min to 1 h at room temperature. The detected proteins were visualized using an ECL kit in accordance with the manufacturer's (Amersham Life Science, RPN 2106) instructions.

1.9 Immunofluorescence

Cells were cultured on cover slips and infected with HSV or rHSV at an MOI of 1. 24 h after infection, the cover slips were washed 3× with PBS (phosphate-buffered saline solution), incubated for 5 min in ice-cooled methanol and then washed once again with PBS. For blocking, the cover slips were incubated in PBS containing 10% NCS for 30 min. The cover slips were then incubated with the respective detection antibodies (see 1.8), which were normally diluted 1:1 in PBS containing 10% NCS, for 1 h in a moist chamber. After having been washed three times with PBS, the cover slips were incubated for a further 30 min with diluted fluorescein isothiocyanate (FITC)-labelled anti-mouse antibody. After three further steps of washing with PBS, the cover slips were analyzed using a fluorescence microscope.

1.10 Preparing rAAV

The conventional method (cotransfection), and the rHSV/AAV system according to the invention, were used for preparing rAAV vectors. The experiments were carried out using BHK-21 cells which had been infected either with wild-type HSV type 1 strain 1802 or with the rHSV/AAV according to the invention. Use is made of an rAAV-GFP (UF5), which expresses the GFP (green fluorescence protein) reporter protein (Zolotukhin et al., J. Virol. 70 (1996), 4646–4654). The plasmid preparations, which contained the rAAV genome flanked by the terminal repeat units, were tested for their integrity as regards the terminal repeats before they were used in the experiments.

BHK-21 cells, which were cultured on 5.5 cm dishes, were transfected, in the case of the conventional method, with 10 µg of rAAV-GFP (UF5) plasmid DNA and 10 µg of ΔTR DNA (rep/cap-expressing plasmid) or, in the case of the process according to the invention, only with 10 µg of rAAV-GFP (UF5) DNA. After having been incubated overnight at 37° C. and 5% $CO_2$, the cells were washed twice with serum-free G-MEM and once with PBS before complete G-MEM medium was added. The cells were then infected, for from 6 to 12 h, either with wtHSV-1 1802 at a MOI of 1 (conventional method) or rHSV/AAV at MOIs of from 0.01 to 1 (process according to the invention). After adsorption for one hour at 37° C., the cells were washed once with PBS, after which complete G-MEM was added. The infected cells were incubated at 37° C. and 5% $CO_2$ until CPE was complete (normally from 2 to 3 days). For harvesting, the dishes were frozen at –80° C. and, after thawing, the cells were transferred into a 15 ml tube. After two further cycles of freezing in liquid nitrogen and thawing, the cell debris was removed by centrifuging for 15 min at 1500×g and 4° C. The clear supernatant was collected as the crude lysate and the helper virus was inactivated by incubating at 56° C. for from 15 to 30 minutes. The lysate was either analyzed directly or subjected to further purification on a CsCl gradient.

1.11 Determining the Number of Physical rAAV Particles

The number of physical rAAV particles was determined by means of a dot blot analysis. 20 µl of 10×DNase I reaction buffer (500 mM tris-Cl, pH 7.5; 100 mM $MgCl_2$; 500 µg of BSA/ml), 5 µl of DNase I (12 U) and 170 µl of $H_2O$ were added to 5 µl of the rAAv-containing sample, obtained either from a CsCl gradient fraction or a crude lysate. After incubating at 37° C. for 1 h, 200 µl of 2×proteinase K buffer (20 mM tris-Cl, pH 8.0, 20 mM EDTA, pH 8.0, 1% SDS) and 100 µg of proteinase K were added. After a further incubation at 37° C. for 1 h, a 1/10 volume of 3 M sodium acetate (pH 9.2) was added and the samples were subjected to phenol extraction (1×phenol, 1×phenol/CIA, 1×CIA). After adding 40 µg of glycogen and 2.5 volumes of 100% ethanol, the samples were incubated at –80° C. for 30 min. Finally, the DNA was pelleted by centrifuging for 30 min at maximum speed. The pellets were washed once with 70% ethanol, dried and finally resuspended in 400 µl of 0.4 M NaOH, 10 mM EDTA solution.

As standard, two-fold serial dilutions of rAAV vector DNA (from 40 to 0.3 125 ng of plasmid) were prepared in a volume of 20 µl, to which 0.4 NaOH, 10 mM EDTA solution was added. All the samples were incubated at 100° C. for 5 minutes and immediately cooled on ice. Using a dot blot device, the samples were transferred onto Gene Screen-Plus membranes (NEN Light Science Products), and the DNA was crosslinked on the filters using UV light. The hybridization was carried out as described by Church et al., see above, at 65° C. in 0.25 M sodium phosphate buffer, pH 7.2, 1 mM EDTA, 7% SDS and 1% BSA. After from 30 min to 2 h of prehybridization, the membranes were hybridized overnight to the [α-$^{32}$P]dCTP-labelled 731 bp NotI fragment of rAAV-GFP. The filters were washed three times with washing buffer I (20 mM sodium phosphate buffer, pH 7.2; 2.5% SDS; 0.25% BSA; 1 mM EDTA) and a further three times with washing buffer II (20 mM sodium phosphate buffer, pH 7.2; 1% SDS, 1 mM EDTA), all at 65° C. After the filters had been exposed on X-ray films, the spots were cut out and analyzed in a scintillation counter. The number of physical particles was calculated using the double-stranded rAAV plasmid DNA as standard.

1.12 Determining the Infectious Titer of rAAV Preparations by Means of a Replication Center Assay For carrying out a replication center assay, the cells were harvested before rAAV is released from the cell which is primarily infected and a second infection spreads through the culture. Approximately 5×10$^4$ HeLa cells were added per well to a 12-well plate. After the plate had been incubated overnight, the cells were infected either with adenovirus (MOI=20) on its own, in order to detect wtAAV, or with adenovirus (MOI=20) and wtAAV (MOI=4) in order to detect rAAV. After 1 h of adsorption, the cells were washed and infected with 100 µl of rAAV-GFP-containing lysate. 1 ml of fresh medium was then added after 1 h. The cells were then incubated at 37° C. and 5% $CO_2$ for 24 h and pelleted by centrifugation. Cells which were still adhering were trypsinized and combined with the pelleted cells. The cells were resuspended and transferred to nitrocellulose filters using a vacuum device. The nitrocellulose filters were hybridized in a formamide solution (5×SSC; 50% formamide; 5×Denhardt; 50 mM sodium phosphate buffer, pH 7.2; 0.1% SDS; 0.1 mg of yeast tRNA/ml) at 42° C. either with the [α-$^{32}$P]dCTP-labelled 731 bp NotI fragment from rAAV-GFP or with the [α-$^{32}$P]dCTP-labelled 1465 bp fragment from AAV rep.

2. Results 2.1 Preparing Recombinant HSV/AAV

The starting material used was the HSV type I mutant 1082 (Rixon et al., J. Gen. Virol. 71 (1990) 2931–2939), which only contains one unique XbaI site at position 143 969 (numbering in accordance with McGeoch et al., see above) in the Us region. This position is suitable for integrating heterologous sequences since, on the one hand, no open reading frames are affected and, on the other hand, none of the 5 genes which are located in this region is essential for virus replication in cell culture. The procedure for preparing rHSV is shown in FIG. 1.

psub201lac was cleaved with XbaI in order to excise the complete 8.4 kb expression cassette. The gel-purified expression cassette was then ligated into the XbaI site of HSV-1 1802. To do this, the HSV DNA was digested completely with Xba. 1 µg of the XbaI-cleaved HSV DNA was ligated, in a volume of 20 µl, to 1 µg of purified XbaI fragment from psub201lac. The ligated HSV 1802/psub201lac was transfected into BHK-21 cells using the following procedure: 1 ml of HBS, 1 µl of herring sperm DNA (10 µg/µl) and 10 µg of ligated HSV 1802/psub201lac (1 µg) were mixed together. 70 µl of 2 M $CaCl_2$ were then added dropwise. The solution was poured onto BHK cells after removing the growth medium. After incubating at 37° C. for 40 min, 4 ml of complete G-MEM (containing 5% NCS) were added and the cells were incubated for a further 200 min. After the medium had been removed, the cells were washed once with serum-free G-MEM. The transfected cells were then treated with 1 ml of 20% DMSO in HBS at room temperature for 4 min. The DMSO solution was removed and the cells were washed once again with serum-free G-MEM. After G-MEM containing 5% NCS had been added, the cells were cultured for 3 days until plaques became visible and the virus was then harvested. CRV and CAV were isolated as described in 1.2.

CAV plaque assays were carried out as described in 1.6. The plaques which were visible after 3 days were isolated and transferred into 20 µl PBS containing 5% NCS. After 3 cycles of freezing and thawing, the suspension was used to infect cells, which were then analyzed for the presence of the recombinant herpes simplex virus by means of β-Gal staining and expression of the adeno-associated virus proteins rep or cap. A positive plaque was selected and purified by further subsequent plaque assay rounds. Even when a homogeneous and pure recombinant isolate was already obtained after round 4, further rounds of plaque purification were carried out in order to avoid even the slightest contamination with residual wild-type herpes simplex virus. All the positive plaques exhibited identical patterns of rep or cap expression in the Western blot analysis.

The presence of wild-type HSV was investigated by infecting cell culture dishes of different sizes with the recombinant virus and then staining with X-Gal at approximately 12 h postinfection. When this was done, it was not possible to observe any formation of wild-type HSV, as indicated by unstained regions of infected cells.

It was possible to culture the recombinant HSV, in this document also termed rHSV/AAV, in BHK-21 roller bottles up to CRV titers of from 1 to $2\times10^7$ PFU/ml, as compared with approximately $1\times10^8$ PFU/ml when wild-type HSV-1 1802 was used. The purity of all the rHSV/AAV preparations was analyzed by staining with X-gal (see 1.7). Even when rHSV/AAV was replicated over several rounds, using very low multiplicities of infection, no reversion of recombinant HSV to wild-type HSV was observed. Under these experimental conditions, any wild-type HSV which was present would overgrow the rHSV/AAV, which, as is evident from the above titer data, is at a slight growth disadvantage. At the same time, the isolated rHSV/AAV is stable and able to replicate. Aliquots of the rHSV/AAV preparations were deposited in the European Collection of Cell Cultures CAMR, Salisbury, Wiltshire SP4 0IG, UK, on 10 Nov. 1997 and were given the provisional access number V97111302.

2.2 Expressing AAV Rep Proteins in rHSV/AAV-Infected BHK Cells

Figure 2:
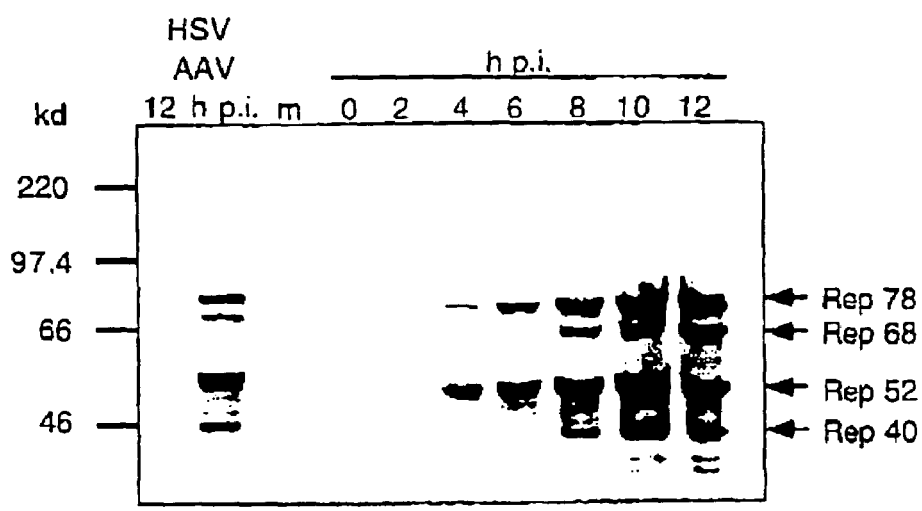
FIG. 2 shows the expression of AAV Rep proteins shortly (A) or long (B) after an infection of BHK cells with rHSV/AAV.
Figure 2:
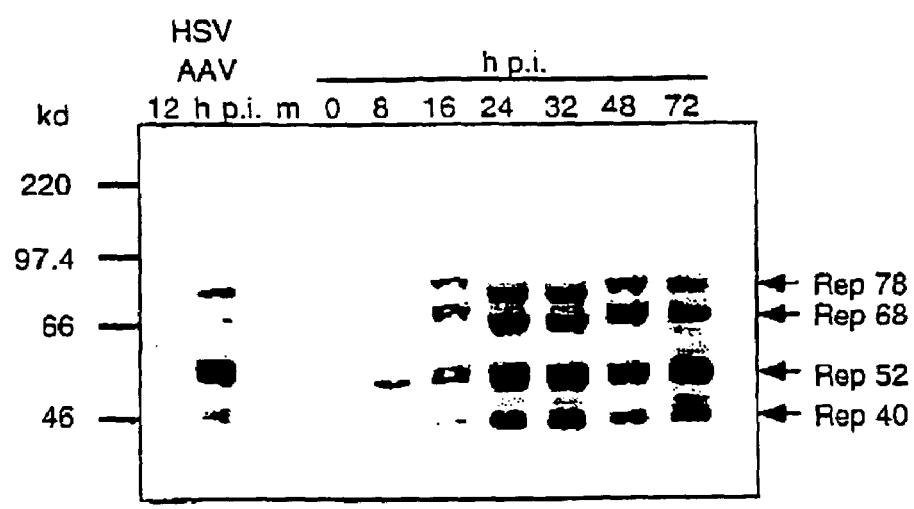

It was already evident in connection with the analysis carried out during the plaque purification that AAV proteins are expressed after cells have been infected with rHSV/AAV. In order to analyze the time course and the level of expression more precisely, BHK-21 cells were infected with rHSV/AAV at a multiplicity of infection (MOI) of 1 and then harvested at the given times after the infection. AAV Rep78 and Rep52 were already detectable in BHK-21 cells four hours after infection with rHSV/AAV (FIG. 2A). At 8 h after infection (8 h p.i.), all four Rep proteins were visible, with the proportions being comparable to a coinfection with AAV wild type and HSV-1 1802. The Rep proteins were expressed at a very high level, with this level being in a range achieved by a productive wild-type AAV infection in the presence of a helper virus.

This result shows that the integrated AAV sequence, which contains the authentic AAV promoters, is regulated by the HSV-specific proteins in the same way as an unintegrated wild-type genome following coinfection with a helper virus. In addition, the results show that a productive HSV life cycle is not significantly inhibited even by a very high content of Rep proteins.

Since an infection with HSV takes over the metabolism of the host cell very rapidly and the cell finally lyses, the presence of Rep proteins was investigated at a late stage in the infection. The result (FIG. 2B) indicates that the expression of Rep proteins reaches a plateau between 16 and 24 h p.i. and that Rep can still be detected even at a very late stage (72 h) after infection.

2.3 Expressing Cap Proteins

Figure 3:
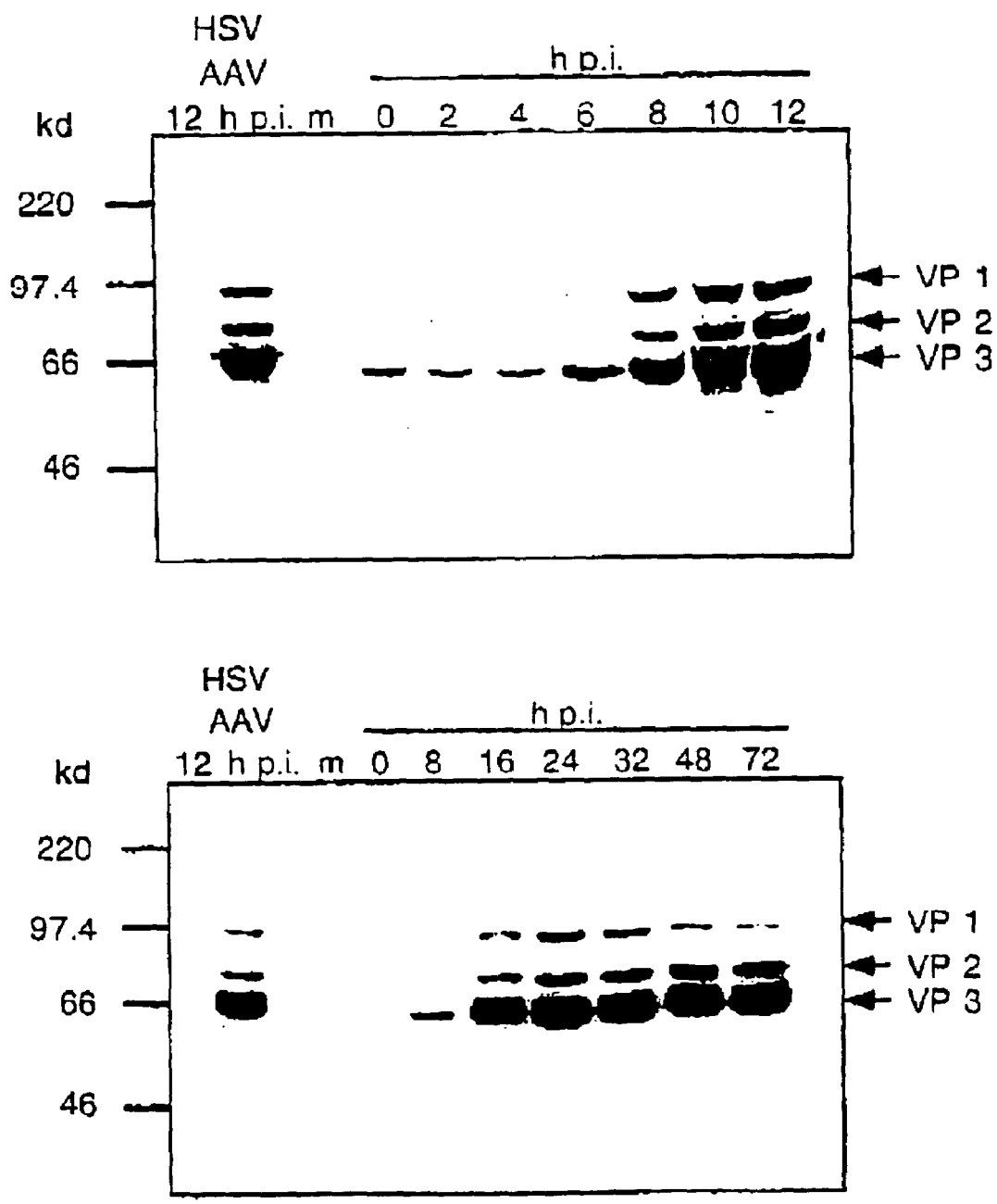
FIG. 3 shows the expression of AAV Cap proteins shortly (A) or long (B) after an infection of BHK cells with rHSV/AAV.

A high level of expression of the adeno-associated Cap proteins is required for efficient packaging. The time course of the expression of AAV Cap in BHK-21 cells following infection with rHSV/AAV was therefore analyzed (FIG. 3). The AAV VP3 protein was already detectable 0 h after infection (FIG. 3A), thereby enabling it to be incorporated into the rHSV/AAV virion. The AAV VP proteins were found to accumulate between 6 and 8 h p.i., with the quantities of VP1, VP2 and VP3 not being distinguishable from a wild-type AAV infection in the presence of HSV-1 at 12 h after infection (FIG. 3A). In this connection, a corresponding expression of the AAV VP proteins was only initiated when the concentration of Rep proteins, in particular Rep78 and Rep52, in the infected cells was sufficient (FIG. 2A). The VP proteins were expressed at a high level from infection and up to 72 h after infection (FIG. 3B).

In summary, it can be stated that high quantities of the VP proteins, whose proportions are comparable with those of a coinfection of wild-type AAV and HSV-1, are present after BHK-21 cells have been infected with rHSV/AAV.

The AAV proteins cap and rep were also found to be expressed in HeLa cells or Vero cells which were infected with rHSV/AAV.

2.4 Detecting AAV Capsid Structures

Figure 4:
FIG. 4 shows the use of immunofluorescence to locate Rep or Cap proteins and assembled AAV capsids in rHSV/AAV-infected BHK cells.
Figure 4:
Figure 4:

An immunofluorescence analysis was used to investigate whether expression of the AAV Cap proteins VP1, VP2 and VP3 is adequate for packaging. An intense nuclear and cytoplasmic staining of rHSV/AAV-infected BHK-21 cells was observed when a Rep-specific antibody (1.8) was used (FIG. 4). A similar staining pattern, with somewhat lower intensities, was found when a Cap-specific antibody (1.8) was used (FIG. 4). It was also possible to detect positive signals in rHSV/AAV-infected cells when the AAV capsid-specific antibody A20 (1.8) was used (FIG. 4).

2.5 Packaging Recombinant Adeno-Associated Virus Vectors with the Aid of rHSV/AAV Recombinant HSV/AAV supports the replication and packaging of recombinant adeno-associated virus vectors, as was shown using lacZ- or GFP-transducing adeno-associated vectors.

In order to determine the actual number of particles, BHK-21 cells or Vero cells were transfected with rAAV-GFP (UF5) or rAAV-GFP and ΔTR and then infected with either rHSV/AAV or HSV-1 1802, as described above. The number of particles in the crude lysate was determined by dot blotting. $1\times10^4$ rAAV-GFP particles were formed per cell when the rHSV/AAV according to the invention was used, as compared with $8\times10^3$ particles per cell when the conventional method was used.

For this, 14 cm culture dishes were transfected with 100 µg of UF5 or 50 µg each of UF5 and ΔTR. The transfected cells were infected with either the recombinant HSV/AAV or the HSV-1 variant 1802 at an MOI of 1. Lysates were prepared three days p.i. and analyzed for the number of physical rAAV-GVP particles. The membrane was hybridized with the [$\alpha$-$^{32}$P] dCTP-labelled 731 bp NotI fragment from rAAV-GFP in a hybridization buffer (Church et al.

Proc. Natl. Acad. Sci. (USA) 81, (1984) 1991–1995) and incubated at 65° C. After washing, the filter was exposed and the spots were cut out. The spots were counted in a Packard scintillation counter and the number of particles was calculated using the standard.

The results are presented in the following table.

TABLE 1

| Sample | Number of cells | Number of rAAV particles | rAAV particles/cell |
|---|---|---|---|
| BHK × UF5 inf. rHSV/AAV | $4 \times 10^7$ | $4 \times 10^{11}$ | $1 \times 10^4$ |
| BHK × UF5/ΔTR inf. HSV-1 | $4 \times 10^7$ | $3.2 \times 10^{11}$ | $8 \times 10^3$ |
| Vero × UF5 inf. rHSV/AAV | $3 \times 10^7$ | $9.5 \times 10^{10}$ | $3.2 \times 10^3$ |
| Vero × UF5/ΔTR inf. HSV-1 | $3 \times 10^7$ | $4 \times 10^{11}$ | $1.3 \times 10^4$ |

2.5 Purity and Stability of the rHSV/AAV Preparation

It is not unusual for wild-type AAV (wt AAV) to be formed during production of an AAV vector (see, for example, Muzyczka, Curr. Topics. Microbiol. Immunol. 158 (1992) 97–129), and this has, therefore, to be checked carefully in association with packaging. The formation of wild-type AAV must be restricted and controlled, in particular when an attempt is being made to prepare a vector on a large scale. The AAV sequences integrated into rHSV/AAV were constructed in such a way that they were free of any elements of the inverted terminal repeat (ITR) sequences. As a consequence, there are no sequence overlaps between rHSV/AAV and the AAV-GFP (UF5) employed, thereby minimizing the possibility of a recombination event which could lead to the formation of wtAAV. In order to exclude the possibility of wtAAV being formed by other processes, e.g. nonhomologous recombination, a crude packaging lysate was analyzed for infectious rAAV-GFP and wtAAV in a replication center assay. In contrast to the dot blot, which measures physical particles, the replication center assay only indicates the particles which are infectious and capable of replication.

Two different concentrations of UF5 (10 μg or 20 μg) or 10 μg each of UF5 and ΔTR were transfected into $4 \times 10^5$ HeLa cells using the Ca phosphate method. At about 20 h after transfection, the cells were infected with rHSV at an MOI of 1 (in the case of UF5 on its own) or adenovirus at an MOI of 3 (in the case of UF5/ΔTR). The cells were harvested at 40 h p.i. and subjected to three freezing/thawing cycles. After incubating at 56° C. for 30 min (in order to inactivate the helper virus), the cell debris was pelleted by centrifugation and the clear supernatant was collected. In order to carry out the replication center assay, HeLa cells which were being cultured in 12-well plates were infected either only with adenovirus (MOI=20) or with adenovirus (MOI=20) and wtAAV (MOI=4). The cells were then infected with 100 μl of each of the previously prepared crude lysates. 24 h later, the cells were harvested, resuspended and transferred to nitrocellulose membranes using a vacuum device. The filters were hybridized with a gfp-specific probe in order to detect rAAV-infected cells and, in parallel with this, with a rep-specific probe in order to visualize cells which were infected with newly formed wtAAV.

Figure 5:
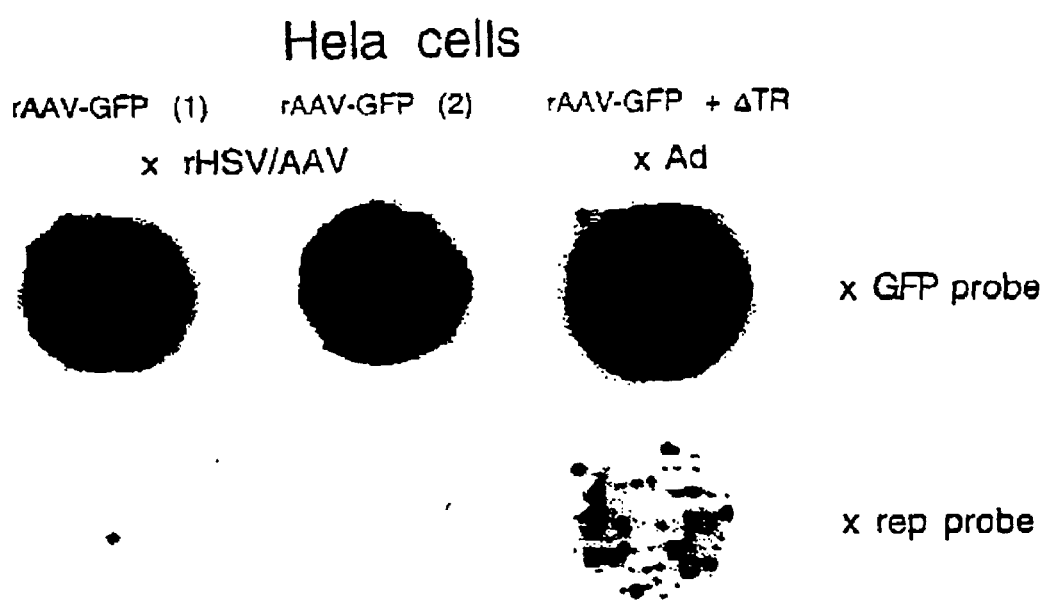
FIG. 5 shows the result of a replication center assay in which the conventional process and the process according to the invention are compared.

The results show that the use of rHSV/AAV together with UF5 is sufficient in order to form recombinant AAV vectors which are competent for an infection with adenovirus, in a similar manner to the conventional cotransfection with UF5 and ΔTR (FIG. 5). The use of either adenovirus-infected or adenovirus- and wtAAV-infected HeLa cells indicates the formation of wild-type AAV. In this experiment, the formation of wtAAV was very high when the conventional method was used. In contrast, virtually no wtAAF particles were formed by the novel rHSV/AAV preparation, as is indicated by hybridization to the rep-specific probe. This was also confirmed by Southern blotting analysis, which failed to find any replicated forms of wtAAV in a variety of packaging preparations.

2.7 Preparing Infectious rAAV-GFP Particles by Infecting with rHSV/AAV

The titer of infectious rAAV-GFP particles was determined. This is normally about $1 \times 10^3$ lower than the number of physical particles. For this, crude lysates prepared from Ca phosphate-transfected BHK-21 cells were analyzed using the infectious titer assay in 96-well plates.

In order to determine the infectious titers of wtAAV or rAAV, HeLa cells were added to 96-well plates at a volume of 90 μl/well. 10 μl of the AAV-containing preparation were added to the wells of the first row and admixed, and the mixtures were then diluted serially 10-fold for each of the following seven steps. After having been incubated for from 12 to 24 h, the transfected cells were infected with adenovirus (MOI=10–20) on its own, in order to analyze for wtAAV, or with adenovirus (MOI=10–20) and wtAAV (MOI=4) when the rAAV titer is being determined. When the cells exhibited a complete CPE, they were frozen and thawed three times. The infectious cell lysates were transferred to a Gene Screen® membrane. After the membrane had been denatured for 5 min on a moist layer of Whatman paper soaked in 0.5 M NaOH, 1.5 M NaCl, and then neutralized by incubating it in 20×SSC/0.5 M Tris, pH 7.5, for 5 min, the DNA was UV-crosslinked on the membrane. The membranes were used for hybridizing with the appropriate probe as described by Church et al., see above, and the rAAV titer or wt AAV titer was calculated.

Figure 6:
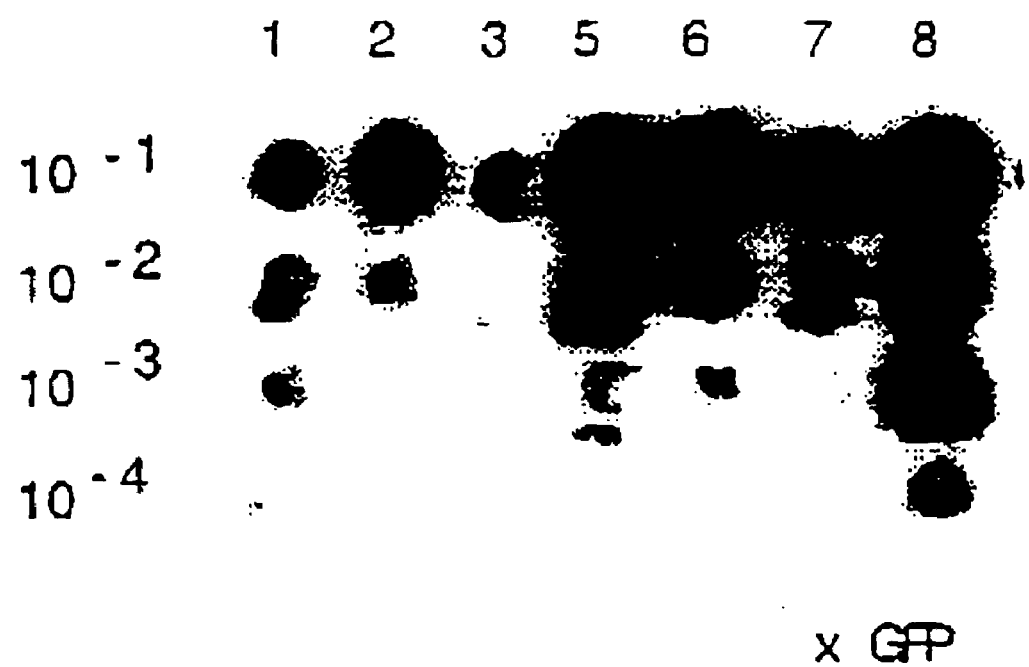
FIG. 6 shows the result of an infectious titer assay of rAAV/GFP in crude lysates.

The results are presented in FIG. 6 and summarized in table 2.

TABLE 2

| Method | 10 μg of UF5, rHSV/AAV MOI = 1 | 10 μg of UF5, rHSV/AAV MOI = 0.1 | 10 μg of UF5, rHSV/AAV MOI = 0.01 | 20 μg of UF5, rHSV/AAV MOI = 1 | 20 μg of UF5, rHSV/AAV MOI = 0.1 | 20 μg of UF5, rHSV/AAV MOI = 0.01 | 10 μg of UF5/10 μg of ΔTR, HSV-1 1802 MOI = 1 |
|---|---|---|---|---|---|---|---|
| inf. rAAV/ml | $1 \times 10^5$ | $1 \times 10^4$ | $1 \times 10^4$ | $1 \times 10^5$ | $1 \times 10^5$ | $1 \times 10^4$ | $1 \times 10^6$ |

What is claimed is:

1. A process for preparing a recombinant herpes virus (rHV) comprising the steps:

preparing an expression cassette that includes an adeno-associated virus (AAV) rep and an AAV cap gene each operably linked to a promoter;

integrating said cassette into a herpes virus (HV) genome to obtain rHV; and replicating the rHV in a host cell without reversion to the corresponding HV sequence lacking AAV rep and cap gene sequences under replication conditions as determined subsequent to at least 3, 5, or 7 dilution steps by a plaque assay.

2. The process of claim 1 wherein the expression cassette optionally lacks all or part of AAV inverted repeat sequences (ITRs).

3. The process of claim 1 wherein the cassette is integrated into the Us or $U_L$, region of the HV genome.

4. The process of claim 1 wherein the herpes virus lacks gene UL9.

5. The process of claim 1 wherein the HV is selected from the group of Herpesviridae consisting of herpes simplex virus (HSV), cytomegalovirus (CMV), pseudorabies virus (PRV), Epstein-Barr virus (EBV) and other herpesvirus family members.

6. The process of claim 1 wherein the HV is identified as a herpes simplex virus (HSV).

7. The process of claim 1 wherein the HV is the recombinant HSV-1 having ECACC accession number V97111302.

8. The process of claim 1, wherein the rep and cap genes are integrated into the HV genome by restriction cleavage/ligation or by homologous recombination.

9. The process of claim 1 wherein the rHV further comprises a selected heterologous gene of interest operably linked to a promoter comprised within the expression cassette.

10. The process of claim 1 wherein the host cell is a mammalian cell.

11. The process of claim 9 wherein the heterologous gene of interest encodes a therapeutically active polypeptide.

12. The process of claim 10 wherein the mammalian cell is selected from the group consisting of HeLa, BHK21 and Vero cells.

13. A recombinant herpes virus having ECACC accession number V97111302.

14. A recombinant herpes simplex virus prepared from HSV-1 strain 1802 by insertion of an expression cassette comprising AAV rep and cap genes each operatively linked to a promoter into an XbaI unique restriction site of said strain 1802.

* * * * *